(12) United States Patent
Müller et al.

(10) Patent No.: US 7,157,253 B2
(45) Date of Patent: Jan. 2, 2007

(54) METHOD FOR THE PRODUCTION OF (R)- AND (S)-8-CHLORO-6-HYDROXYOCTANIC ACID ALKYL ESTERS BY ENZYMATIC REDUCTION

(75) Inventors: Michael Müller, Jülich (DE); Wolfgang Sauer, Dresden (DE); Gunter Laban, Dresden-Langebrück (DE)

(73) Assignee: Viatris GmbH & Co. KG, Bad Homburg (DE)

( * ) Notice: Subject to any disclaimer, the term of this patent is extended or adjusted under 35 U.S.C. 154(b) by 0 days.

(21) Appl. No.: 10/493,630

(22) PCT Filed: Oct. 14, 2002

(86) PCT No.: PCT/EP02/11470

§ 371 (c)(1), (2), (4) Date: Oct. 5, 2004

(87) PCT Pub. No.: WO03/035885

PCT Pub. Date: May 1, 2003

(65) Prior Publication Data

US 2005/0032180 A1 Feb. 10, 2005

(30) Foreign Application Priority Data

Oct. 23, 2001 (DE) ................. 101 52 113

(51) Int. Cl.
*C12P 11/00* (2006.01)
(52) U.S. Cl. ..................................... 435/130
(58) Field of Classification Search ................. 435/130
See application file for complete search history.

(56) References Cited

FOREIGN PATENT DOCUMENTS

| DE | 19533882 | | 3/1997 |
|---|---|---|---|
| EP | 0939132 | | 9/1999 |
| EP | 939132 | * | 9/1999 |
| WO | 0210422 | | 2/2002 |

OTHER PUBLICATIONS

Fronza et al., J. Org. Chem, vol. 56, 1991, pp. 6019-6023.*
Tsuboi et al., J. Org. Chen., vol. 63, 1998, pp. 1102-1108.*
Ema et al., J. Org. Chem., vol. 66, pp. 8682-8694, 2001.*
Fronza et al, "On the Mode of Bakers' Yeast Transformation of 3-Chloropropiophenone and Related Ketones," J. Org. Chem, vol. 56, 1991, pp. 6019-6023.
Tsuboi et al, "Highly Enantioselective Synthesis of Both Enantiomers of gamma-substituted butenolides by Bakers' Yeast Reduction and Lipase-Catalyzed Hydrolysis," J. Org. Chem, vol. 63, 1998, pp. 1102-1108.
Ema et al, "High Enantioselectivity and Broad Substrate Specificity of a Carbonyl Reductase," J. Org. Chem, vol. 66, 2001, pp. 8682-8684.
Kleemann und Engel, "Pharmaceutical Substances," 1999, pp. 1860-1861.

* cited by examiner

*Primary Examiner*—Deborah D. Carr
(74) *Attorney, Agent, or Firm*—Ann S. Hobbs; Venable LLP

(57) ABSTRACT

The invention relates to a method for the production of (R)- or (S)-8-chloro-6-hydroxyoctanoic acid alkyl esters of the general formula (R)-II or (S)-II

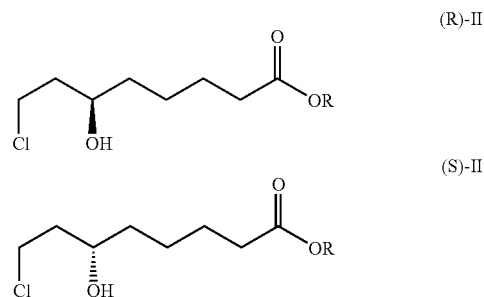

in which R has the meaning $C_{1-4}$-alkyl, from 8-chloro-6-oxooctanoic acid alkyl esters of the general formula I

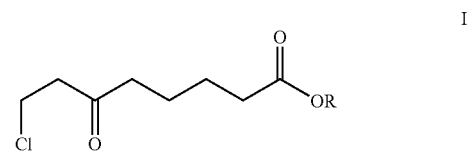

in which R has the above meaning, by enzymatic reduction using alcohol dehydrogenases, such as *Lactobacillus brevis* or *Thermoanaerobium brokii*, in the presence of cofactor regeneration systems.

The resulting (R)- and (S)-8-chloro-6-hydroxyoctanoic acid esters can be converted in a known manner into (R)-α-lipoic acid and (S)-α-lipoic acid, respectively.

5 Claims, No Drawings

METHOD FOR THE PRODUCTION OF (R)- AND (S)-8-CHLORO-6-HYDROXYOCTANIC ACID ALKYL ESTERS BY ENZYMATIC REDUCTION

The invention relates to a method for the production of (R)- and (S)-8-chloro-6-hydroxyoctanoic acid alkyl esters of the formula I by enzymatic reduction of a suitable prochiral keto compound.

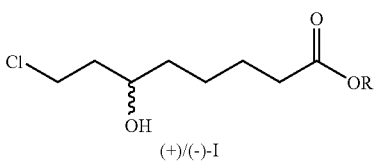

(+)/(-)-I

R = alkyl

The synthesis of α-lipoic acid on the industrial scale starts from 8-chloro-6-oxooctanoic acid alkyl esters, which are converted by NaBH$_4$ reduction into 8-chloro-6-hydroxyoctanoic acid alkyl esters (reference: Kleemann and Engel, Pharmaceutical Substances, 3rd Ed., Thieme, 1999, p. 1860). A subsequent three-stage synthetic sequence results in the racemic α-lipoic acid in a high overall yield. Besides the synthesis of racemic α-lipoic acid, also of great importance is the synthesis of the pure enantiomers for specific pharmaceutical use (concerning this, see, for example EP 04 27 247). It is appropriate to carry out the synthesis of the pure enantiomers in analogy to the established economic method for synthesizing the racemic active ingredient. Accordingly, various methods have been developed to prepare the enantiopure intermediates, see, inter alia, DE-A-19533882. Enantio-selective reductions of prochiral ketone compounds to chiral secondary alcohols, which lead as intermediates in alternative synthetic routes to enantiopure α-lipoic acids, are to be found in DE-A-197 09 069. All the methods involve multistage synthetic sequences, some of which are associated with complicated purification operations or else are based on racemate resolution (DE 4137773), leading to the maximum yield of an enantiomer being 50%—without recycling by racemization or inversion. The low overall yield of these methods make them appear economically unrewarding. None of the described methods is based on a direct, one-stage preparation of an enantiopure intermediate of the established economic method for synthesizing racemic α-lipoic acid.

The object of the invention was thus to indicate a method for the production of certain intermediates for producing (R)- and (S)-α-lipoic acid and of (R)- and (s)-α-lipoic acid itself, which makes it possible to produce these compounds and the intermediates with high yield and high enantiopurity.

This object is achieved by enzymatic reduction of 8-chloro-6-oxooctanoic acid alkyl esters using alcohol dehydrogenases or carbonyl reductases. This conversion results in either the (R) or (S)-8-chloro-6-hydroxyoctanoic acid alkyl ester of the formula (R)-II or (S)-II indicated in the claim.

The invention derives from the realization that the employed initial ester can be reduced in a simple manner and very effectively using known alcohol dehydrogenases or carbonyl reductases.

There are certain indications in the literature that dehydrogenases might be suitable for synthesizing chiral compounds (see, inter alia, Kragl and Kula, in. Stereoselective Biotransformations, editor R. Patel, Marcel Dekker, 2000, pages 839–866). However, the general statements in this and similar references cannot be applied to complex starting compounds. The worry for the skilled worker in this connection is ordinarily side reactions and reduced enantioselectivity. Thus, only one example of the biocatalytic reduction of the chloroethyl ketone could be found in the literature (Mele at al., J. Org. Chem. 1991, 56, 6019). In this case, a chloroethyl aryl ketone is reduced to the chiral secondary alcohol by whole-cell biotransformation (Saccharomyces cerevisiae). The reduction proceeds with neither high chemoselectivity nor high enantioselectivity. In the reduction of chloroethyl ketones with biocatalysts which, as in the case of compounds of the formula I, have a second bulky substituent, it is not possible to predict, owing to the large spatial demands of the substituents, whether a particular biocatalyst will accept such a compound as substrate.

J. Org. Chem. 66, 8682–84 (2001) reveals that an 8-chloro-3-hydroxyoxtanoic acid alkyl ester can be obtained by reduction from the corresponding ketone with purified carbonyl reductase and whole cells. EP 0 939 132 A1 discloses an enzymatic reduction of 4-halo-3-ketobutyric acid esters. J. Org. Chem. 63, 1102–08 (1998) describes the reduction of 3-chloro-4-ketooctanoic acid ethyl esters. EP 0 487 986 A2 discloses obtaining (3S)-3-hydroxyoctanedioic acid diesters for preparing lipoic acid by reduction with baker's yeast.

Surprisingly, various alcohol dehydrogenases and carbonyl reductases show high acceptance of compounds of the formula I as substrate (analytical assay), and it has been possible to confirm this in preparative conversions.

The invention is indicated more precisely in claim 1 and further dependent claims. In the conversion of the invention, generally known cofactors are employed, such as, for example, NAD(H), NADP(H), FADH$_2$. NAD(H) or NADP(H) is preferably used.

The configuration of the resulting 8-chloro-6-hydroxyoctanoic acid alkyl esters is determined by the enzyme employed. Thus, reduction of 8-chloro-6-oxooctanoic acid alkyl esters using alcohol dehydrogenase from *Thermoanaeorubium brokii* results in enantiopure (R)-8-chloro-6-hydroxyoctanoic acid alkyl esters. In the case of reduction using *Lactobacillus brevis* alcohol dehydrogenase, there is enantioselective formation of (S)-8-chloro-6-hydroxyoctanoic acid alkyl esters (ee>65%). Enzymes which show an activity with the compounds of the formula I as substrate are listed in the table below.

The enzymes are commercially available.

The starting compounds for preparing the intermediates, the prochiral 8-chloro-6-oxooctanoic acid alkyl esters, can be obtained in a known way (L. J. Reed et al., J. Am. Chem. Soc. 1955, 774, 416).

Y-ADH yeast alcohol dehydrogenase
HL-ADH horse liver ADH
READH *Rhodococcus erythropolis* ADH
CPCR *Candida parapsilosis* carbonyl reductase
CBADH *Candida boidinii* ADH
LKADH *Lactobacillus* kefir ADH
LEADH *Lactobacillus* brevis ADH
TEADH *Thermoanaerobium brokii* ADH
TEA triethanolamine
Tris trishydroxymethylaminomethane
Kpi mixture of monopotassium phosphate and dipotassium phosphate
DTT dithiothreitol

| Enzyme | Cofactor | Buffer | Cosubstrate/ Coenzyme | Activity/ (conversion) | Standard |
|---|---|---|---|---|---|
| Y-ADH | NAD(H) | 100 mM TEA, pH 7.0 | | 20% | 2-butanone |
| HL-ADH | NAD(H) | 100 mM TEA, 1 mM MgCl$_2$ pH 7.0 | | <1% | methyl aceto-acetate |
| READH | NAD(H) | 100 mM glycyl-glycine, pH 6.5 | | 2% | methyl aceto-acetate |
| CBADH | NAD(H) | 50 mM Kpi, pH 6.5 | (30° C.) | 60% | acetone |
| CPCR | NAD(H) | 100 mM TEA, pH 7.8 | (HCO$_2$Na, FDH) | 60% | methyl aceto-acetate |
| LKADH | NADP(H) | 50 mM Kpi, 0.1 mM MgCl$_2$, pH 7.0 | iso-propanol 200 mM | 10% (36%) | aceto-phenone |
| LBADH | NADP(H) | 50 mM Kpi, 1 mM MgCl$_2$, pH 6.5 | iso-propanol 200 mM | 6% (>25%) | methyl aceto-acetate |
| TBADH | NADP(H) | 50 mM Tris, 1 mM DTT, pH 7.8 | HCO$_2$Na, FDH (37° C.) | 6% (>85%) | 2-butanone |

For preparative conversions it proves advantageous to include a cofactor regeneration system in the enzymatic biotransformation. Cofactor regeneration systems which prove to be particularly advantageous are those which shift the equilibrium of the main reaction. Thus, for example in the case of reductions with *Lactobacillus brevis* alcohol dehydrogenase, a substrate-coupled co-factor regeneration in the presence of an excess of a secondary alcohol (e.g. 2-propanol) is possible and advantageous. Alternatively, enzyme-coupled cofactor regeneration systems (e.g. formate dehydrogenase (FDH)/formate) can be employed, and can be utilized for the reduction of NAD(P) to NAD(P)H. The CO$_2$ resulting from the oxidation of the cosubstrate sodium formate escapes as gas and is thus removed from the equilibrium. Both NAD- and NADP-dependent formate dehydrogenases are described in the literature and commercially available.

The present invention makes it possible to obtain the (R)- and (S)-8-chloro-6-hydroxyoctanoic acid alkyl esters of the formula I in a simple and economic manner in high chemical and optical yield (theoretically 100% chemical and optical yield) in a one-stage method.

The invention also relates to the use of the enantiopure octanoic acid alkyl esters obtained in the method of the invention for producing (R)- or (S)-α-lipoic acid in a manner know per se. In the known methods, the chlorohydroxyoctanoic acid alkyl esters are normally converted into the corresponding dichlorooctanoic acid alkyl esters. The known lipoic acid structure is then obtained in a further reaction step by introducing sulfur.

As an example of the enantioselective production of an 8-chloro-6-hydroxyoctanoic acid alkyl ester in accordance with the present invention, the following scheme shows the production of enantiopure (R)-8-chloro-6-hydroxyoctanoic acid methyl ester.

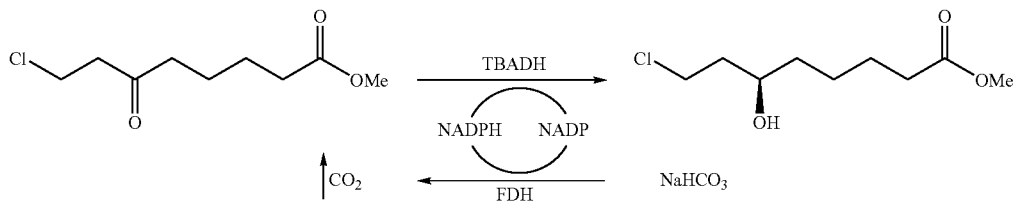

The absolute configuration of the optical isomers of 8-chloro-6-hydroxyoctanoic acid alkyl esters of the formula I was determined by comparison with the signs of the specific optical rotations with literature data (Gewald et al., DE 195 33 881). In addition, the relative contents of the optical isomers of the 8-chloro-6-hydroxyoctanoic acid alkyl esters of the formula I was found by GC on columns with chiral phase with a limit of detection of <0.5%.

(S)-8-Chloro-6-hydroxyoctanoic acid alkyl esters are obtainable in an analogous manner by employing as biocatalyst for example *Lactobacillus brevis* alcohol dehydrogenase. The synthesis of (+)- and (−)-α-lipoic acids starting from (+)- and (−)-8-chloro-6-hydroxyoctanoic acid alkyl esters can be carried out in accordance with known methods. The invention is illustrated in detail by the following example.

EXAMPLE 1

100 mg (0.5 mmol) of 8-chloro-6-oxooctanoic acid methyl ester (substrate), dissolved in 50 ml of 50 mM TRIS buffer pH 7, containing 0.1 mM DTT and 0.5 mM NADP, are mixed with in each case 2 U/mg (substrate) TBADH and FDH (NADP-dependent) and stirred at 37° C. Workup by standard methods affords enantiopure (ee>99.5%) (R)-8-chloro-6-hydroxyoctanoic acid methyl ester (product).

The invention claimed is:

1. A method for the production of (R)-S-chloro-6-hydroxyoctanoic acid alkyl esters of the formula (R)-II,

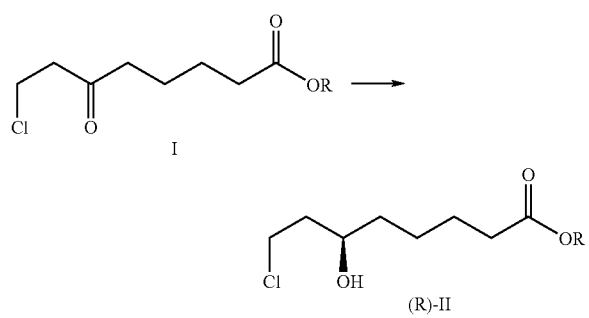

in which R has in each case the meaning $C_{1-4}$-alkyl, characterized in that 8-chloro-6-oxooctanoic acid alkyl esters of the formula I are reduced enzymatically using alcohol dehydrogenases or carbonyl reductases in the presence of NAD(H) or NADP(H) as cofactor.

2. A method for the production of (S)-8-chloro-6-hydroxyoctanoic acid alkyl esters of the formula (S)-II,

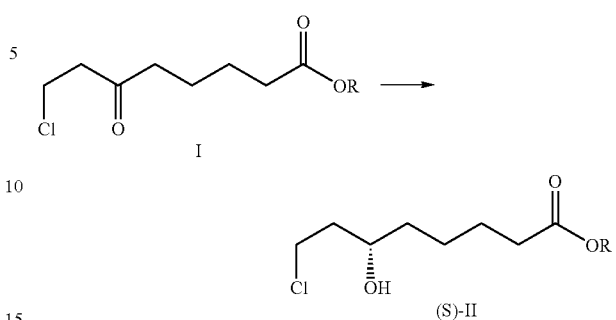

in which R has in each case the meaning $C_{1-4}$-alkyl, characterized in that 8-chloro-6-oxooctanoic acid alkyl esters of the formula I are reduced enzymatically using alcohol dehydrogenases or carbonyl reductases in the presence of NAD(H) NADP(H) as cofactor.

3. The method as claimed in claim 1, characterized in that an alcohol dehydrogenase from *Thermoanaerobium brokii* is employed.

4. The method as claimed in claim 2, characterized in that an alcohol dehydrogenase from *Lactobacillus brevis* is employed.

5. The method as claimed in according to one of claims 1–4, characterized in that a cofactor regeneration system which shifts the reduction equilibrium is included in the enzymatic reduction.

* * * * *